United States Patent
Andrade (10) Patent No.: US 12,383,392 B2
(45) Date of Patent: Aug. 12, 2025

(54) ARTIFICIAL BLADDER

(71) Applicant: Ernesto Andrade, Miami Beach, FL (US)

(72) Inventor: Ernesto Andrade, Miami Beach, FL (US)

(*) Notice: Subject to any disclaimer, the term of this patent is extended or adjusted under 35 U.S.C. 154(b) by 788 days.

(21) Appl. No.: 17/659,245

(22) Filed: Apr. 14, 2022

(65) Prior Publication Data

US 2022/0331087 A1 Oct. 20, 2022

Related U.S. Application Data

(60) Provisional application No. 63/201,141, filed on Apr. 14, 2021.

(51) Int. Cl.
*A61F 2/04* (2013.01)
*A61F 2/48* (2006.01)

(52) U.S. Cl.
CPC .............. *A61F 2/042* (2013.01); *A61F 2/48* (2021.08); *A61F 2220/0075* (2013.01)

(58) Field of Classification Search
CPC ...... A61F 2/042; A61F 2/0009; A61F 2/0022; A61F 2/48; A61F 2002/048; A61M 2210/1078; A61M 2210/1085; A61M 2210/1089
USPC ...................................................... 623/23.65
See application file for complete search history.

(56) References Cited

U.S. PATENT DOCUMENTS

| | | | |
|---|---|---|---|
| 4,311,659 A | 1/1982 | Rey et al. | |
| 4,961,747 A | 10/1990 | Wascher et al. | |
| 5,370,690 A * | 12/1994 | Barrett | A61F 2/042 |
| | | | 623/23.65 |
| 7,131,996 B2 | 11/2006 | Wasserman et al. | |
| 9,044,310 B2 | 6/2015 | Sambusseti | |
| 9,393,099 B2 | 7/2016 | Sambusseti et al. | |
| 11,202,700 B1 | 12/2021 | Pettlon, Sr. et al. | |
| 2019/0091003 A1* | 3/2019 | Forsell | A61F 2/0036 |
| 2019/0388212 A1 | 12/2019 | Ha et al. | |
| 2021/0353402 A1* | 11/2021 | Ha | A61F 2/482 |

* cited by examiner

*Primary Examiner* — Jerrah Edwards
*Assistant Examiner* — Savannah J. Herring
(74) *Attorney, Agent, or Firm* — Schwegman Lundberg & Woessner, P.A.

(57) ABSTRACT

An implantable medical device for use as an artificial urinary bladder can include a collection container configured to be placed in a patient's abdominal cavity and a pump configured to be subcutaneously placed outside the abdominal cavity to allow the patient to perceive the need for urination and controls timing of the urination. Flexible tubing can connect the patient's ureters to the collection container, connect the collection container to the pump, and connect the pump to the patient's urethra, with unidirectional valves where needed, to allow for urination through the patient's natural urethra. The implantable medical device can optionally include a cleaning port and tubing connecting the cleaning port to the collection container for introducing a liquid cleaning agent into internal urination circuit of the device for cleaning, disinfection, and prevention of stone formation.

20 Claims, 11 Drawing Sheets

ARTIFICIAL BLADDER

CLAIM OF PRIORITY

This application claims the benefit of priority under 35 U.S.C. § 119(e) of U.S. Provisional Patent Application Ser. No. 63/201,141, filed on Apr. 14, 2021, which is herein incorporated by reference in its entirety.

TECHNICAL FIELD

This document relates generally to implantable medical devices and more particularly, but not by way of limitation, to an implantable medical device that can be used as an artificial bladder for collecting and discharging urinary fluids.

BACKGROUND

The urinary bladder (referred to as "urinary bladder" or "bladder" herein) is a hollow muscle-membranous organ that is part of a person's urinary tract. The bladder receives urine from the ureters, stores the urine, and expels the urine from the body of the person through the urethra during urination. The bladder has a spherical shape. In its posterior-superior portion, the bladder connects to the ureters through which the urine is received from the kidneys. In its inferior-medial portion, the bladder terminates in the urethra, which terminates at the urinary meatus. After entering the bladder, the urine accumulates to level that is sensed by pressure corpuscles, which send signals to the brain to initiate urination. Urination is a complex act during which the detrusor muscle contracts while the urethral sphincter relaxes.

Surgical removal of the bladder, a procedure known as radical cystectomy, may become necessary due to various reasons such as certain tumors and trauma. One example of such reasons includes bladder cancer, which is one of the most common types of cancer worldwide and also known as one of the leading causes of death. This necessities the surgical removal of the bladder for many patients. Once a patient's bladder is removed, it is necessary to restore the function previously performed by the patient's bladder, including allowing the urine to accumulate and then flow and discharge at regular intervals out of the patient's body. Currently there is surgical procedure and/or artificial device that can replace the bladder with its full natural functions.

An example of a surgical technique for restoring urinary functions after bladder removal includes harvesting a portion of the patient's intestine, adhering it to the ureters, and subsequently generating a urinary stoma across the abdominal wall. An externally carried urine collection bag is attached to the body to collect the urine through the stoma. There are two ways to manage this technique. One way includes a surgery that takes a portion of the intestine and isolates it from its full length. The remaining portions of the intestine are joined together so that the intestine continues its function. One end of "borrowed" portion of the intestine is closed. The other end is removed from the abdominal cavity through muscles and skin and to form the stoma (artificial opening) on the surface in the patient's abdominal area. The ureters are attached to this "borrowed" portion of the intestine to allow the urine to accumulate in and flow through it to the stoma. A bag is attached to the skin in the abdominal area to cover the stoma to collect the urine. This procedure, known as ureterocutaneostomy, does not restore the natural functions performed by the patient's bladder. For example, the urine does not accumulate properly within the body and is not expelled through the regular duct, the urethra. The other way is substantially the same, except that instead of forming the stoma on the skin, a larger sac is created to form a urinary storage bag. Thus, the patient has to permanently perform catheterization through the urethra to remove the urine.

Another example of a surgical technique for restoring urinary functions after bladder removal includes a surgery for harvesting a portion of the intestine and connect it to the ureters and the urethra to create a neobladder. To create the neobladder, the patient's bladder (e.g., a cancerous or severely traumatized bladder) is removed by a procedure known as a cystectomy, either through a traditional abdominal incision or with a robot-assisted laparoscopic approach (robotic surgery). A segment of the small intestine, a portions of the colon, or a combination of both is remodeled to form a sphere, which becomes the neobladder. The neobladder is placed in the patient's body in the space that was occupied by the original bladder. The neobladder is attached to the ureters so that the urine can drain from the kidneys into the neobladder. The other end of the neobladder joins the urethra. This technique allows the patient to maintain urine control with a functional bladder capable of storing urine without the need for external device (e.g. a bag). However, potential complications can occur with the neobladder construction, such as bleeding, blood clots, infection, urinary leakage, urinary retention, electrolyte imbalances, vitamin B-12 deficiency, incontinence, and cancer in the intestine.

In additional to the great technical difficulty of the procedure, the neobladder is associated with a high morbidity with subsequent complications and a non-negligible mortality rate. Complications have been specifically detected over the years in patients who have undergone the neobladder construction surgery, related to metabolism and liver medications, vitamin deficiency, electrolyte disorders, bone diseases, cancers, and related problems with the presence of an ostomy, such as bleeding, stenosis, and hernia. Furthermore, following the procedure, serious incontinence problems are common, forcing the patient to wear diapers for incontinent adults and hence experiencing physical and psychological discomfort. There are also other types of neobladders known as heterotopic, such as the intestinal neobladder connected to the navel, emptied by the patient through a catheter. This type of neobladder also has drawbacks related to the difficulty of implantation and infections that can cause kidney failure.

Therefore, at this time, patients undergoing bladder removal have the possibility of experiencing a totally unsatisfactory quality of life, which also implies a significant economic cost for the health system. All external urinary components, such as bags, as well as internal components, such as neobladders, involve substantial costs for regular maintenance, which may include multiple controls and replacements performed by specialized personnel.

SUMMARY

An implantable medical device for use as an artificial urinary bladder can include a collection container configured to be placed in a patient's abdominal cavity and a pump configured to be subcutaneously placed outside the abdominal cavity to allow the patient to perceive the need for urination and controls timing of the urination. Flexible tubing can connect the patient's ureters to the collection container, connect the collection container to the pump, and connect the pump to the patient's urethra, with unidirectional valves where needed, to allow for urination through the patient's natural urethra. The implantable medical device can optionally include a cleaning port and tubing connecting the cleaning port to the collection container for introducing a liquid cleaning agent into internal urination circuit of the device for cleaning, disinfection, and prevention of stone formation.

An example of the implantable medical device is provided. The implantable medical device may include: first and second tubes configured to be connected to the ureters to receive the urine from the kidneys through the ureters; a collection container coupled to the first and second tubes and configured to be placed inside the abdominal cavity and to receive the urine from the two tubes; a pump configured to be placed outside of the abdominal cavity; a third tube connected between the collection container and the pump to provide for fluid communication from the collection container to the pump; a first unidirectional valve coupled to the third tube and configured to allow the urine to flow from the collection container to the pump; a fourth tube connected to the pump and configured to be connected to the urethra; and a second unidirectional valve coupled to the fourth tube and configured to allow the urine to flow from the pump to the urethra.

Another example of the implantable medical device is provided. The implantable medical device may include: first and second tubes configured to receive the fluid; a collection container coupled to the first and second tubes and configured to receive the fluid from the two tubes; a pump; a third tube connected between the collection container and the pump to provide for fluid communication from the collection container to the pump; a first unidirectional valve coupled to the third tube and configured to allow the fluid to flow from the collection container to the pump;

a fourth tube connected to the pump; a second unidirectional valve coupled to the fourth tube and configured to allow the fluid to flow from the pump to the fourth tube; a cleaning port configured to receive the liquid cleaning agent; a fifth tube connected between the cleaning port and the collection container to allow fluid communication from the cleaning port to the collection container; and a third unidirectional valve coupled to the fifth tube and configured to allow the liquid cleaning agent to flow from the cleaning port to the collection container.

A method for replacing functions of a urinary bladder using an implantable medical device placed in a body of a patient is also provided. The method may include: collecting urine from kidneys of the living body using a collection container placed within the abdominal cavity through first and second tubes connected between the ureters and the collection container; allowing the urine to flow from the collection container to a pump subcutaneously placed outside of the abdominal cavity through a third tube connected between the collection container and the pump when the pump is not pressed by the patient; and allowing the urine to flow from the pump to the urethra through a fourth tube connected between the pump and the urethra when the pump is pressed by the patient.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense.

The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

FIGS. 4-11 illustrate an embodiment of operations of the implantable medical device of FIG. 1.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, an implantable medical device that can be used as an artificial bladder for placement in the body of a patient to collect and discharge biological urinary fluids. In light of what is discussed in the BACKGROUND section, use of artificial bladder replacement prostheses made with suitable synthetic materials has undoubted advantages. However, despite research efforts in this field, there is still a need for such a device with satisfactory performance in the medium and long terms.

This is mainly due to the fact that despite having highly bio-compatible materials including medical grade silicone, challenges remain in developing an artificial bladder that avoids reflux, contains urine, and then expels the urine through the urethra at times controlled by the patient. Another challenge is the potential formation of a fungal-based microfilm on the interior walls of the artificial bladder that promotes infection and stone formation.

The urine, which is in continuous contact with the material inside the artificial bladder during its use, is a liquid that tends to be acidic, which exposes all kinds of material, to a greater or lesser extent, to the risk of fouling. Use of bioengineered tissues to reconstruction of the bladder have been investigated. Studies used regenerated tissues consisting of autologous patient cells that were cultured in vitro and then seeded in media, such as those made with collagen and polyglycolic acid, to construct organs for implantation. Despite the encouraging results from early experimental use of such regenerated tissues, their extensive clinical use still requires substantial efforts to gain knowledge and make advances in areas such as optimization of the regenerative materials to be used, cellular phenotypes to be selected, fixation and integration of implants in the human body, and so on.

On the other hand, many elastomeric materials have been proposed which exhibit mechanical properties, both static and dynamic, that are suitable for use as a substitute for natural bladder tissue. The present subject matter uses biocompatible materials that are known for reducing rate of potential infection and potential formation of stones and are known for suitability for long-term use with corrosion-resistance to urinary fluids. However, identifying a suitable material is just one of the fundamental goals for developing the implantable medical device for use as the artificial bladder.

In view of the efforts made over the past two decades in the fields of tissue engineering, materials science, and regenerative medicine, it is recognized by the inventor that a new approach to the structural and functional design of the implantable medical device for use as the artificial bladder is critical to restoration of the functions of the genitourinary system for improving the quality of life of the patients after removal of their natural bladders. Goals for this new approach include meeting requirements or desires of this technical field including, but not limited to: ease of implantation in the patient's body, operation based on controllable urine emptying, adequate stability and biocompatibility that allows for long-term use after implantation, protection of normal kidney function, and cost effectiveness.

Pathologies related to the bladder showing its loss of control or inability to contract, such as in the case of the hypotonic bladder or the neurogenic bladder provoke considerations of replacing such lost or impaired functions using mechanical means in the implantable medical device. The inventor also discovered that a function of the natural bladder has been neglected though it seemed obvious, which is the ability of the bladder to notify the brain of the need to urinate based on the volume of the urine accumulated in the bladder. The human brain receives this notification not only through the internal nerves between organs, but also through indoctrinated images. While this function is missing from various existing artificial bladders, the present subject matter incorporates it into the implantable medical device for use as the artificial bladder.

The present subject matter provides an implantable medical device that can be used for replacing a natural organ that has been removed, for example due to cancer, severe trauma, or substantial failure of its function. When being used as an artificial bladder, the present implantable medical device can be made of a biocompatible material that is highly corrosion-resistant to urinary fluids and can have a shape and volume similar to those of the natural bladder.

In various embodiments, the present implantable medical device when used to replace the natural bladder of a patient can have a performance comparable to that of the natural bladder in terms of urine collection, reflux prevention, and expulsion of the collected urine through the patient's urethra. The present implantable medical device can be constructed for long-term corrosion resistance and stability in its intended environment inside the patient's body. Unlike other devices designed for the same or similar functions, the present implantable medical device mobilizes the urine out of the abdomen by means of a suction and expulsion pump operable by light pressure from the patient when desired. The pump is placed subcutaneously to allow the patient to apply pressure to draw the urine collected in a collection container placed in the abdominal cavity and move the urine from the pump back into the abdominal cavity to reach the urethra, which is a final conduit of the natural urination. Thus, the patient is allowed to control when they should and want to urinate and to urinate through the natural urethra, thereby maintaining a good quality of life. In various embodiments, the present implantable medical device is made radiation compatible because, for example, some of the patients may be subjected to radiation therapies. In various embodiments, the present implantable medical device can provide an option of being washed internally and frequently to minimize the risks of microfilm and/or stone formation.

Figure 1:
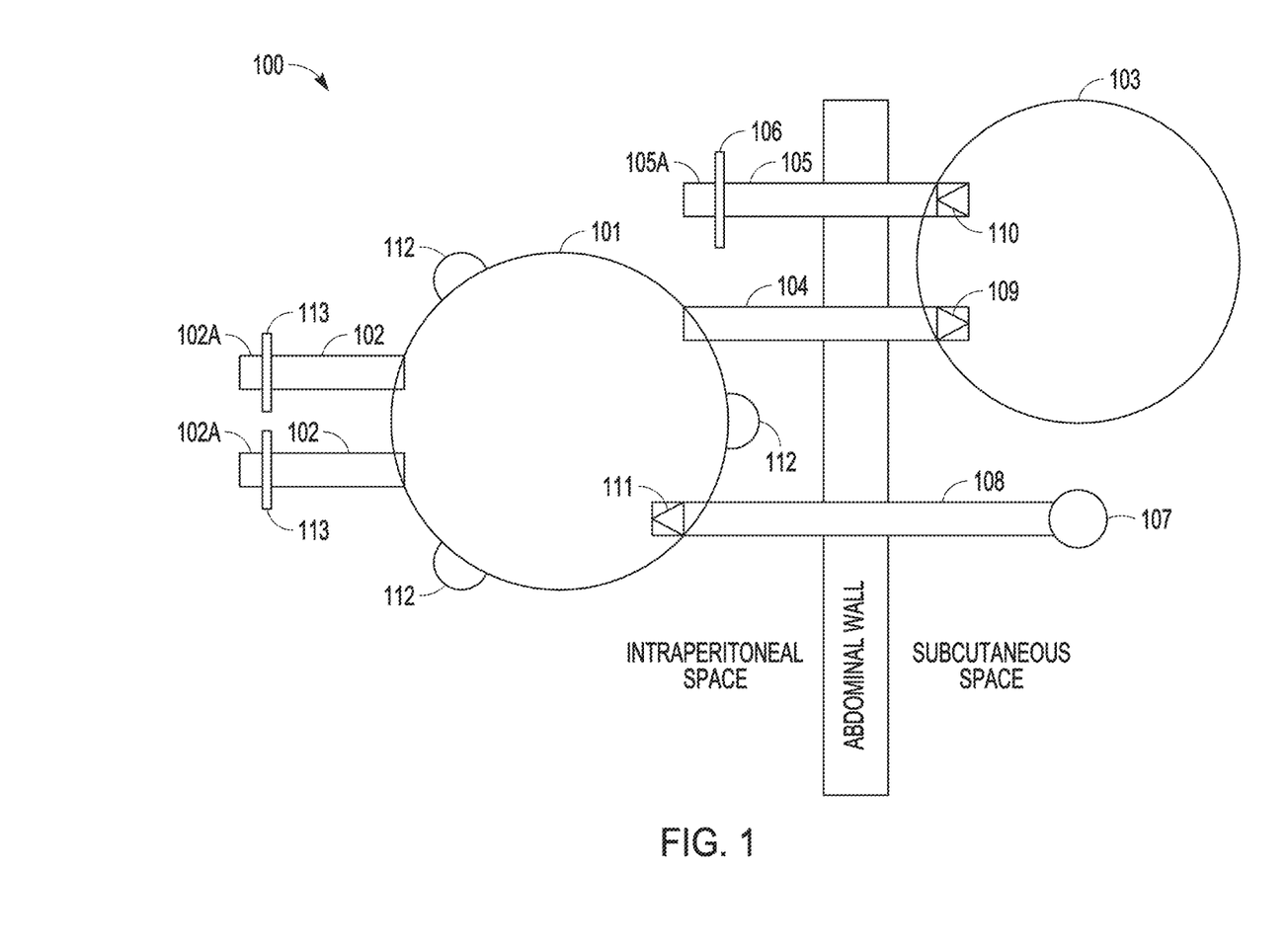
FIG. 1 illustrates an embodiment of an implantable medical device and portions of an environment in which the implantable medical device is used as an artificial bladder.

FIG. 1 illustrates an embodiment of an implantable medical device 100 and portions of an environment in which device 100 is used as an artificial bladder. Implantable medical device 100 can be used to restore functions of the natural bladder of a patient after the natural bladder is removed. To restore the functions of the natural bladder, implantable medical device 100 includes a collection container 101 for collecting urine, flaps 112 (optional, for affixing collection container 101 to tissue), two tubes 102 for connecting the ureters to collection container 101 (each including a portion 102A to be inserted into one of the ureters), two rings 113 (optionally) to secure the connections each between one of tubes 102 and one of the ureters, a pump 103, a tube 104 coupled with a unidirectional valve (also referred to as check valve) 109 for connecting collection container 101 to pump 103, a tube 105 coupled with a unidirectional valve (also referred to as check valve) 110 for connecting pump 103 to the urethra (including a portion 105A to be inserted into the urethra), and a ring 106 (optionally) to secure the connection between tube 105 and the urethra. To allow for internal cleaning, implantable medical device 100 can optionally further include a cleaning port 107 and a tube 108 coupled with a unidirectional valve (also referred to as check valve) 111 for connecting port 107 to collection container 101. Implantable medical device 100 can be made entirely of medical grade silicone. This material is compatible with radiotherapy and shows excellent stability in its relationship with human tissues in the long term.

Figure 2:
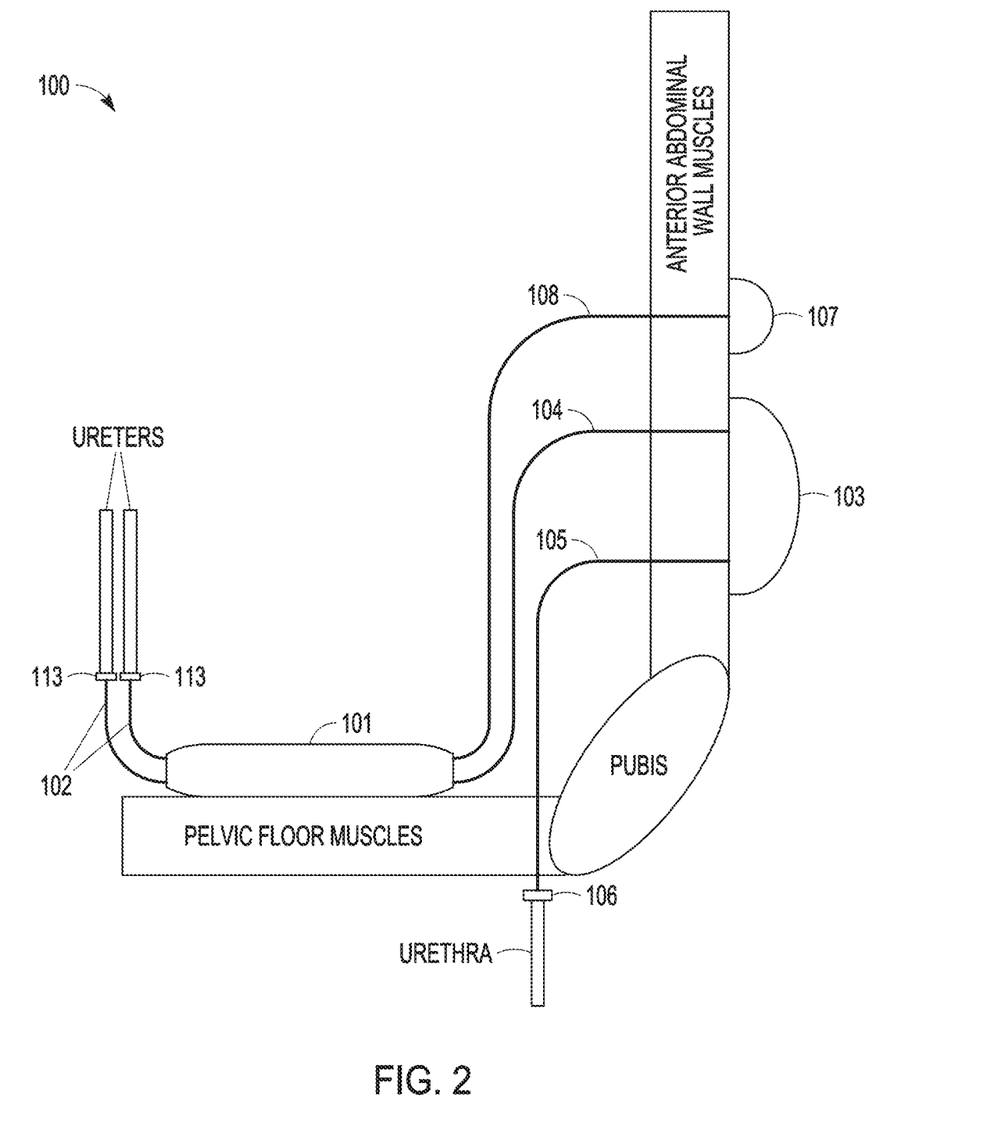
FIG. 2 illustrates an embodiment of the implantable medical device of FIG. 1 showing locations of its components relative to adjacent main anatomical structures of a patient's body after implantation.
Figure 3:
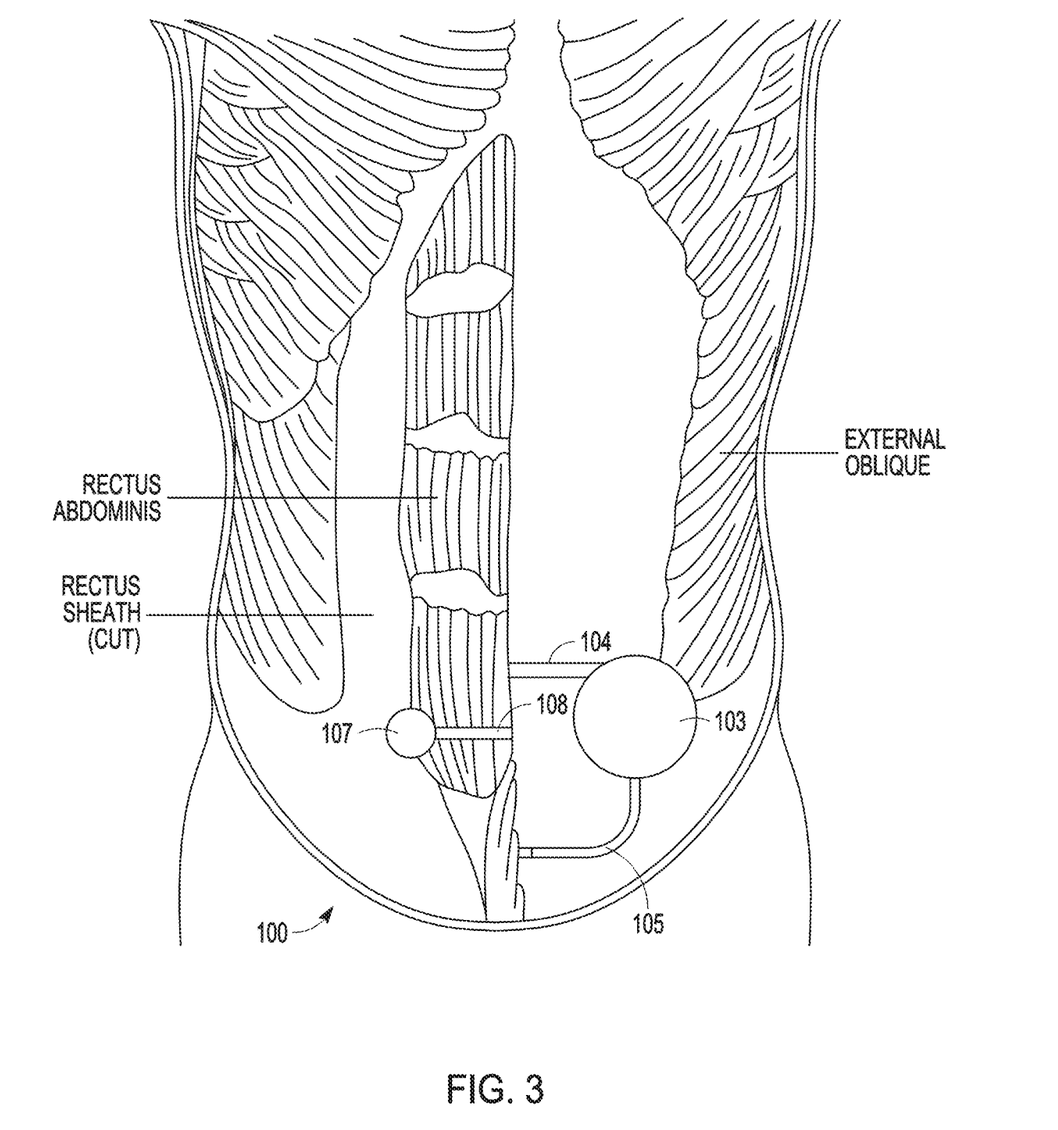
FIG. 3 illustrates an embodiment of the implantable medical device of FIG. 1 showing a pump and a cleaning port of the device placed over abdominal muscles of the patient's body.

FIG. 2 illustrates an embodiment of implantable medical device 100 showing locations of its components relative to main adjacent anatomical structures of the of the patient's body after implantation of implantable medical device 100 into the patient. The anatomical structures shown in FIG. 2 include representations of muscles of the pelvic floor, the pubis (bone), and muscles of the anterior abdominal wall. FIG. 3 illustrates an embodiment of implantable medical device 100 showing its components that are subcutaneously placed between the abdominal wall and the skin, external to the abdominal cavity, after the implantation of implantable medical device 100 into the patient. FIG. 3 shows pump 103 and port 107, with portions of tubes 104, 105, and 108 placed on a portion of the rectus sheath (illustrated with a cutaway portion to show the underneath rectus abdominis) and over portions of the rectus abdominis (and possibly portions of the external oblique). A unique and fundamental characteristic of implantable medical device 100 is that parts of the device are implanted inside the abdominal cavity while other parts of the device are implanted outside the abdominal cavity in the subcutaneous space over the abdominal wall muscles, which allows for patient control of the urination process.

Collection container 101 is a bag having a flexible, elastic hollow body for use as a passive urine container that can have a volume capacity between 100 ml and 350 ml, with approximately 250 ml being a specific example. The volume capacity can be custom selected for the patient. Collection container 101 can have shape and size similar to those of the natural bladder (e.g., a spherical shape or a shape more closely resembling that of the natural bladder) and can be placed within the abdominal cavity, in the space previously occupied by the natural bladder (which has been removed). Thus, collection container 101 can be placed inside the patient's abdominal cavity to resemble the natural anatomical position and structure of the bladder. Affixation features can be incorporated onto collection container 101 to stabilize its position in the abdominal cavity after the implantation of device 100. In one embodiment, as illustrated in FIG. 1, collection container 101 includes flaps 112 that can be sutured to deep tissues (e.g., muscles of the pelvic floor) to minimize displacement of collection container 101 in the abdominal cavity.

Tubes 102 are flexible conduits each have one end coupled to collection container 101 and the other end to be connected to one of the patient's ureters, to provide for fluid communication from the ureters to collection container 101. Collection container 101 receives the urine from the patient's kidneys through the ureters and tubes 102. In this manner, collection container 101 functions as a passive urine container. Rings 113 can each include one or more rings optionally coupled to the respective tube 102 for providing a secure connection between that tube and the respective ureter. For example, when needed, rings 113 can each be sutured to the respective ureter after portion 102A of the respective tube 102 has been inserted into that ureter.

Pump 103 includes an elastic hollow container that can be pressed to function as a pump. This container of pump 103 can have a volume capacity between 50 ml and 350 ml, with approximately 250 ml being a specific example. This volume capacity can be custom selected for the patient when needed. For example, while 250 ml is considered to be sufficient given average normal production of a urination, a larger volume (e.g., 300 ml) can be used if the patient anticipates higher-than-average urine production rate and/or longer urination periods for any reason. The container can have can have a wall that is sufficiently thick to maintain a shape (e.g., a hemispherical shape) after device 100 is implanted. The thickness of the wall can be between 3 mm to 6 mm, with 4 mm being a specific example. Pump 103 is to be subcutaneously placed outside of the abdominal cavity and can be affixed (e.g., sutured) to the fascia of the abdominal muscles. In various embodiments, the wall of a base portion of pump 103 (the flat portion to be attached to the fascia of the abdominal muscles) is substantially thicker than the wall of a hemispherical top portion of pump 103. For example, the wall of the flat base portion of pump 103 can be up to twice as thick as the wall of the hemispherical top portion of pump 103. When the wall of the hemispherical top portion is 4 mm thick, the wall of the flat base portion can be up to 8 mm thick. The thicker flat base portion of pump 103 facilitates exertion of a negative pressure for the pumping function as further discussed below (with reference to FIG. 6).

Tube 104 is a flexible conduit connecting pump 103 to collection container 101 to provide for fluid communication from collection container 101 pump 103. Unidirectional valve 109 is coupled to tube 104 to allow the urine to flow through tube 104 in the direction from collection container 101 to pump 103 only.

Tube 105 is a flexible conduit having one end connected to pump 103 and the other end to be connected to the patient's urethra to provide for fluid communication from pump 103 to the urethra. Unidirectional valve 110 is coupled to tube 105 to allow the urine to flow through tube 105 in the direction from pump 103 to the urethra only. Ring 106 can include one or more rings optionally coupled to tube 105 for providing a secure connection between tube 105 and the urethra. For example, when needed, ring 106 can be sutured to the urethra neck after portion 105A of tube 105 has been inserted into the urethra.

Device 100 can be implanted into the patient with pump 103 producing a spontaneous vacuum sucking the urine from collection container 101 through tube 104 and valve 109. This negative pressure exists until the container of pump 103 reaches its volume capacity and opens unidirectional valve 109 such that the urine can only flow from collection container 101 (functioning as a passive container) to pump 103 (functioning as an active container). The patient can perceive that the urine contained in pump 103 approaches its volume capacity, which is the mechanism of device 100 for notifying the patient to empty the urine. For example, the patient can see and/or fell pump 103 as a bump that looks like a small breast implant when it is full and a small crater when it is empty. Once in the bathroom, the patient can gently press the skin over pump 103 with a hand. This pressure causes valve 109 to close and valve 110 to open, thereby causing the urine in pump 103 to be expelled from the patient through tube 105 and the urethra.

Once the patient finishes urinating, pump 103 can return spontaneously to its starting empty state by producing a slight and continuous vacuum inside it, which closes valve 110 and opens valve 109 when urine again accumulates in collection container 101. All the urine that reaches the intra-abdominally positioned collection container 101 will be constantly sucked into the extra-abdominally positioned pump 103, such that the patient can participate in the urination process in a manner similar to that with the natural bladder. Valves 109 and 110 can each be positioned in an un-collapsible area (e.g., within pump 103) to avoid interference during the suction and expulsion processes of pump 103.

In various embodiments, device 100 optionally includes an internal cleaning mechanism that include cleaning port 107, tube 108, and unidirectional valve 111. Cleaning port 107 includes an elastic container that allows for injecting a liquid cleaning agent into the urination circuit of device 100 through tube 108 and valve 111. Tube 108 is a flexible conduit connecting cleaning port 107 to collection container 101, to provide for fluid communication from cleaning port 107 to collection container 101. Unidirectional valve 111 is coupled to tube 108 to allow the liquid cleaning agent to flow through tube 108 in the direction from cleaning port 107 to collection container 101 only. Valve 111 can be positioned in an un-collapsible area (e.g., within collection container 101).

Cleaning port 107 is to be placed subcutaneously over the abdominal wall such that it is visible and palpable through the abdominal skin after device 100 is implanted. A cleaning procedure can be performed percutaneously by using a thin surgical stainless steel lead (e.g., a hollow needle) to inject the liquid cleaning agent into cleaning port 107. The wall of cleaning port 107 can be self-sealing after being pierced for the injection of the liquid cleaning agent. The liquid cleaning agent can include a substance that changes the pH value of the content inside device 100 to clean and disinfect the interior surfaces of device 100 against potential infection or contamination caused by the residual urinary liquid. An example of the liquid cleaning agent includes a non-irritant mixture of saline solution with sodium hypochlorite and large spectrum antibiotics. Each cleaning process can start with injecting about 100 ml of his solution into cleaning port 107. Once the liquid cleaning agent is injected (and mixed with the urine in collection container 101), the patient can perform the same procedure as in the urination process to complete the cleaning process with the liquid cleaning agent expelled through the urethra. The liquid cleaning agent cleans the interior wall surfaces of all the components of device 100 during the cleaning process.

In various embodiments, unidirectional valves 109, 110, and 111 are each used to prevent the urine from flowing in the wrong direction and/or into a wrong portion of device 100 or the patient (e.g., the kidneys). In various embodiments, while valves 109, 110, and 111 are each coupled to one end of its respective tube, they can each be coupled with to the respective tube in any location for providing the tube with the intended unidirectionality.

Device 100 can be seen as an artificial passive bladder connected to a manually operated active compression pump to collect the patient's urine and allows the collected urine to be controllably expelled through the urethra. A mechanism for cleaning can be included in device 100 when desired, for an easy and convenient way of allowing for periodic maintenance ensuring proper functioning of device 100 during its intended long-term use. In one embodiment, device 100 is constructed and provided for surgical implantation as a single unit. In other embodiments, device 100 is constructed as multiple components that can be assembled prior to and/or during surgical implantation.

In various embodiments, device 100 is made of 100% biocompatible material. Biocompatibility of a material used to construct a device intended to be implanted in a biological system includes acceptable types and degrees of interactions between the material and the host biological system. This includes an appropriate response of the host biological system to the material for a given application of the device, including not interfering or detrimentally interacting with the physiological activities of the host biological system. Interactions between the external surface of device 100 and the surrounding tissue result in minimal inflammatory response.

In various embodiments, the biocompatible material used for constructing device 100 is also reliable for long-term implantation. Such a material is biostable. Once device 100 is implanted, the material does not undergo substantial chemical and/or chemical transformation over time. While "long-term" can include any length of time over 30 days, in various embodiments device 100 is intended for use in the patient for at least 10 years. In various embodiments, a preventive maintenance that can include replacement of device 100 can be performed periodically following the implantation, such as every 10 years, and/or as needed (e.g., indication of device dysfunction or side effect observed).

In various embodiments, the biocompatible material used for constructing device 100 has mechanical properties comparable to these of the natural organ it is intended to replace. For use as the artificial bladder, the material has mechanical properties suitable for supporting the functionality of device 100 including accumulation and discharge of urinary body fluids.

In various embodiments, device 100 is made of materials having the biocompatibility, reliability, and mechanical properties as discussed above. One example of such material is medical grade silicone. In one embodiment, device 100 is entirely made of medical grade silicone.

Figure 7:
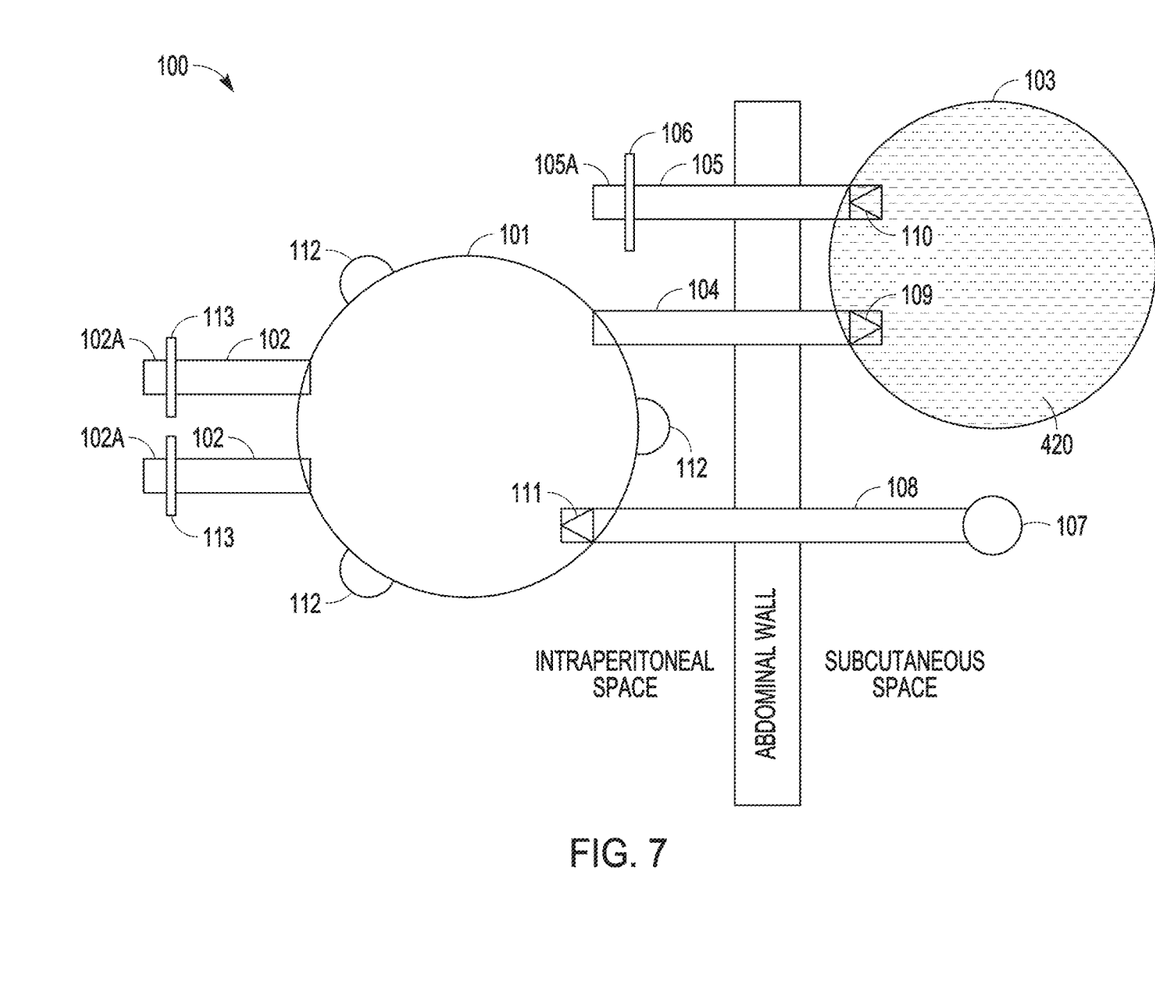
FIG. 7 shows the pump being filled up with the urine.
Figure 8:
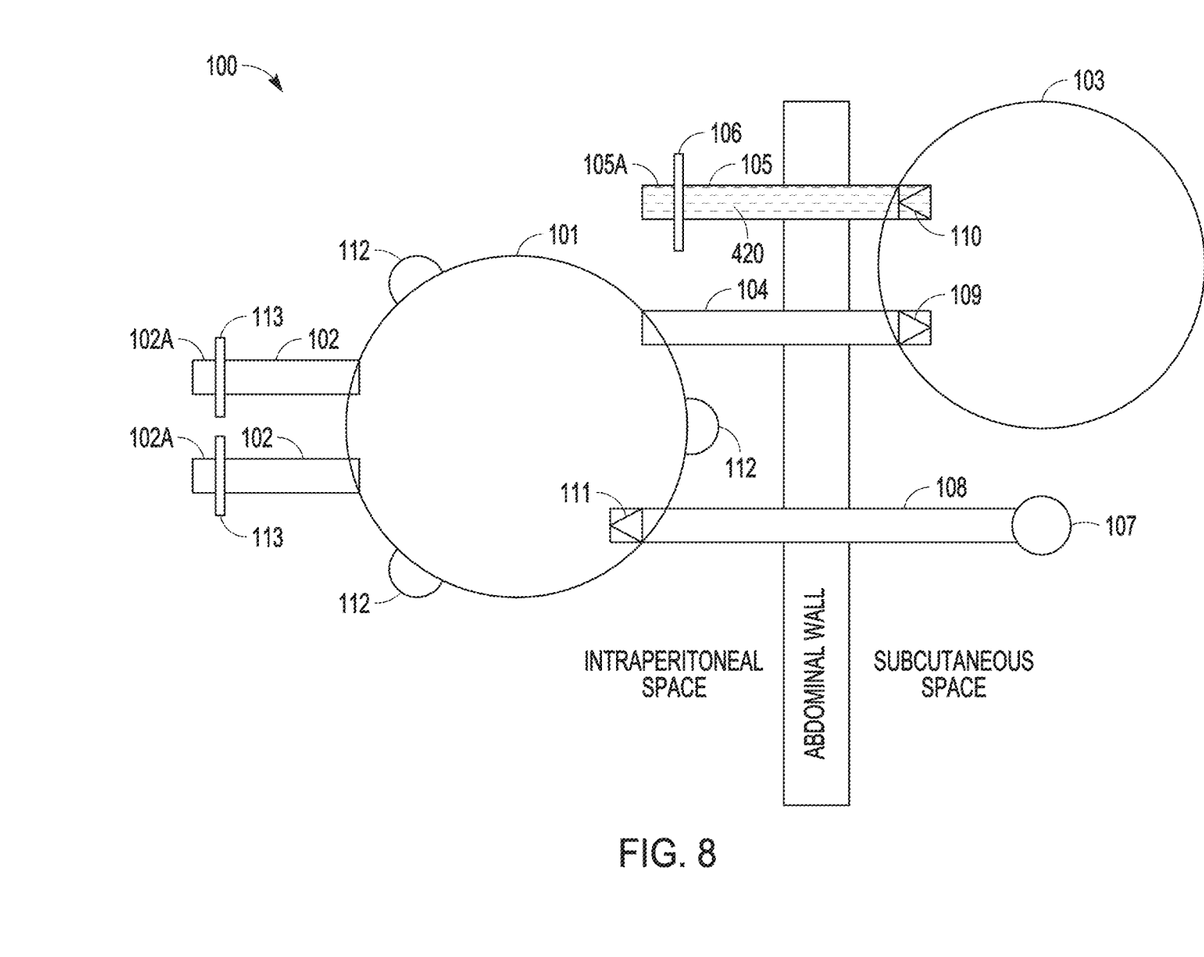
FIG. 8 shows effect of external pressure applied on the pump to allow the urine to exit the pump and flow through a tube that connects the pump to the urethra of the patient for final expulsion of the urine.
Figure 9:
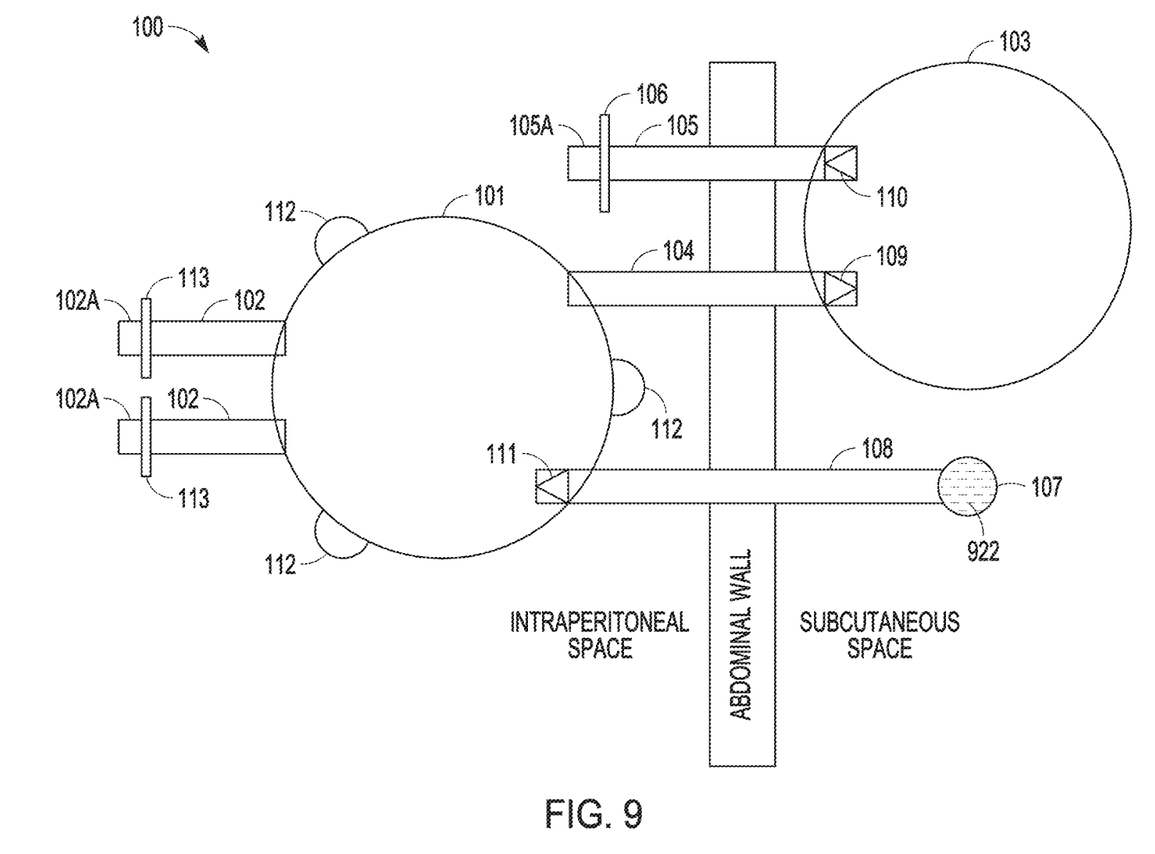
FIG. 9 shows a cleaning port filled with a liquid cleaning agent.
Figure 10:
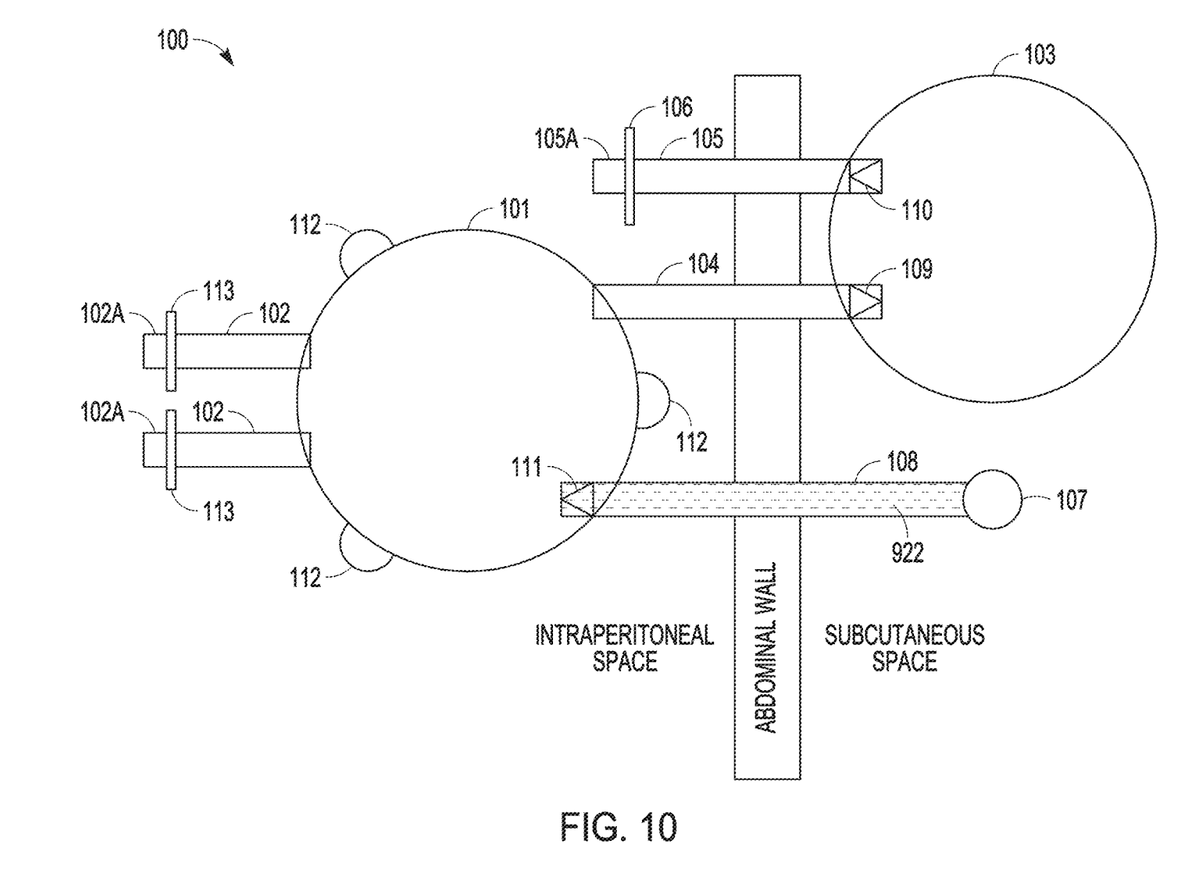
FIG. 10 shows the liquid cleaning agent entering through a tube connecting the cleaning port to the collection container.
Figure 11:
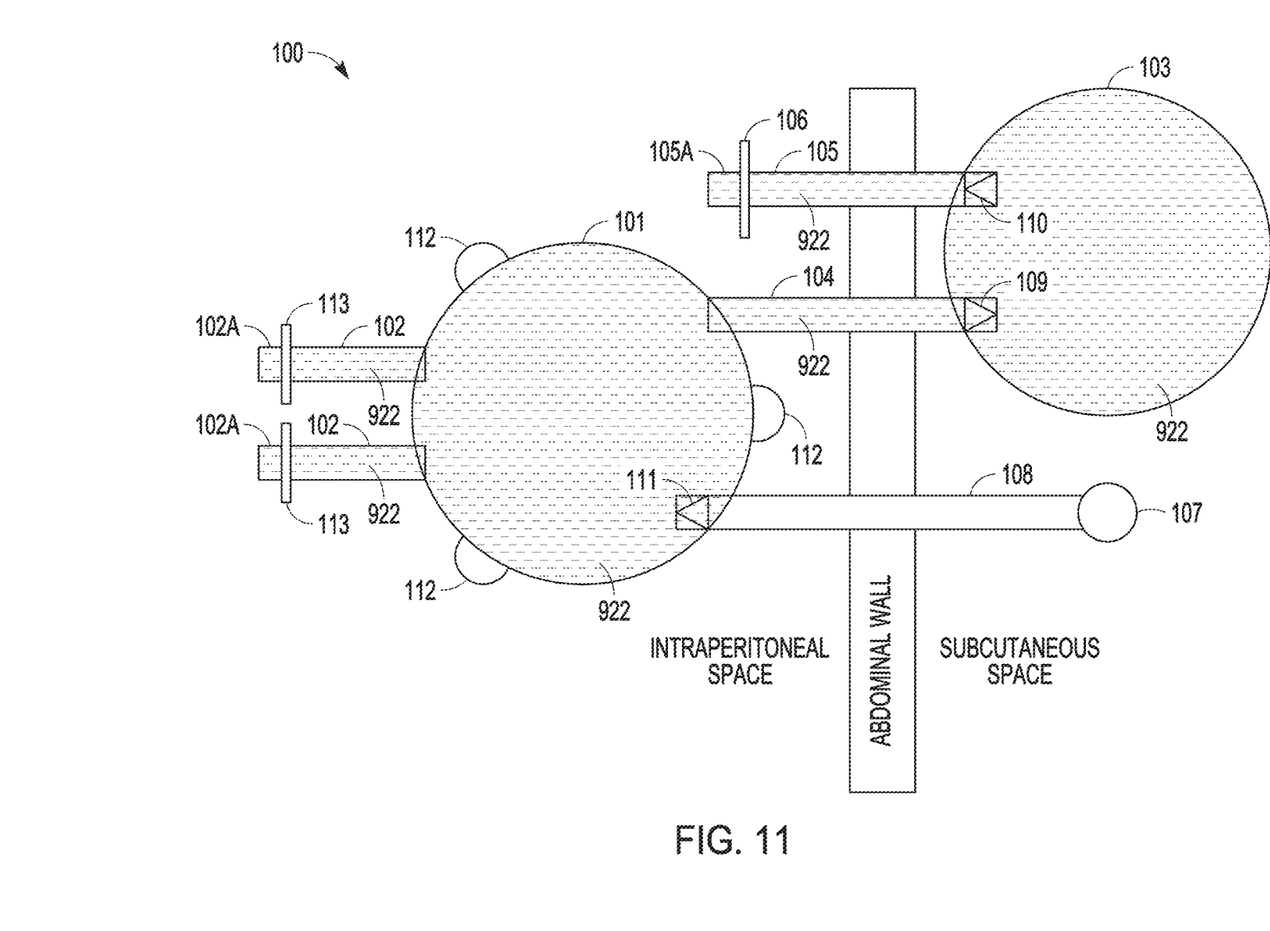
FIG. 11 shows the entire implantable medical device being washed using the liquid cleaning agent.

FIGS. 4-11 illustrate an embodiment of operations of device 100 (including the optional cleaning mechanism), showing a urination cycle (FIGS. 4-8) and a cleaning cycle (FIGS. 9-11). The shaded areas in FIGS. 4-8 indicate where the urine (420) reaches. The shaded areas in FIGS. 9-11 indicate where the liquid cleaning agent (922) reaches.

Figure 4:
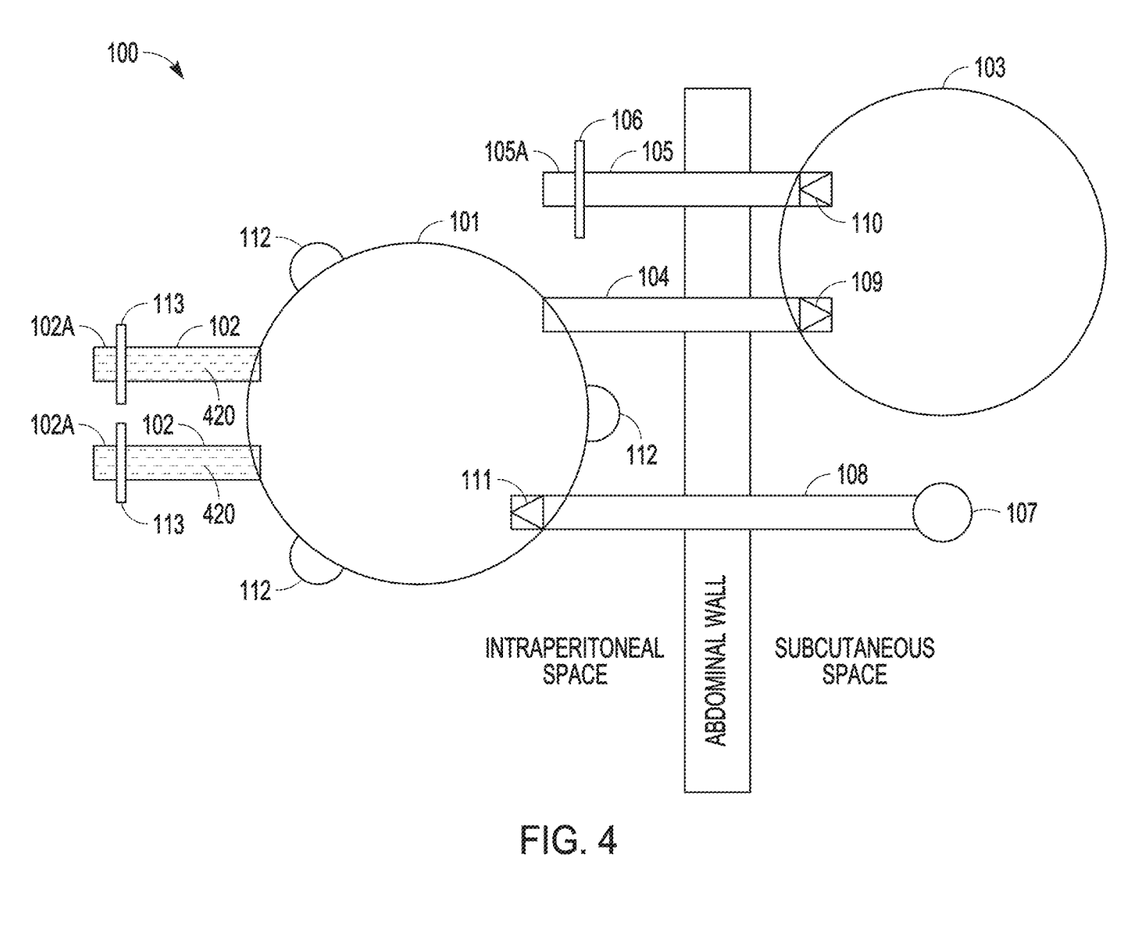
FIG. 4 shows entrance of urine into tubes connected to the patient's ureters.
Figure 5:
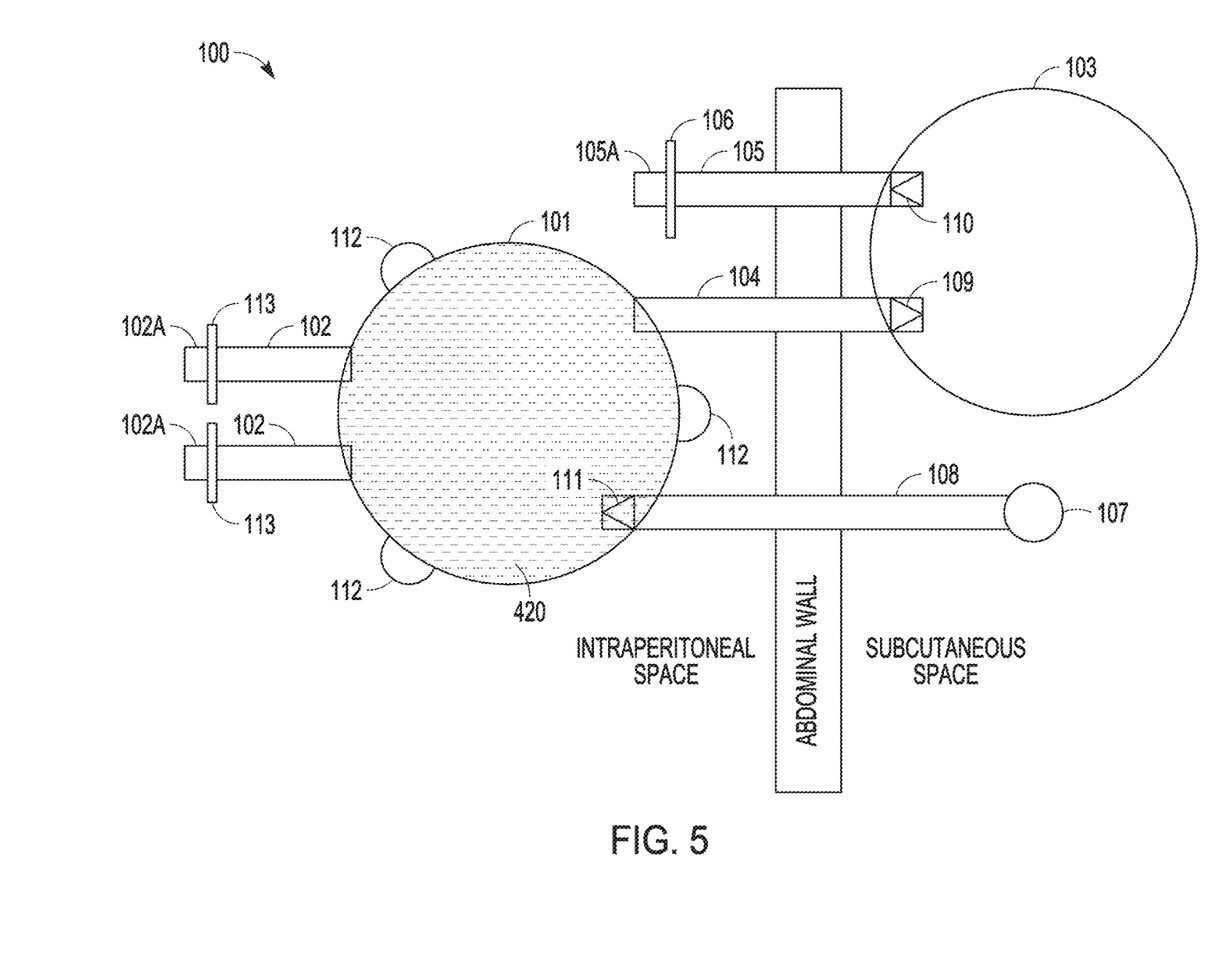
FIG. 5 shows the urine reaches a collection container placed in the patient's abdominal cavity.
Figure 6:
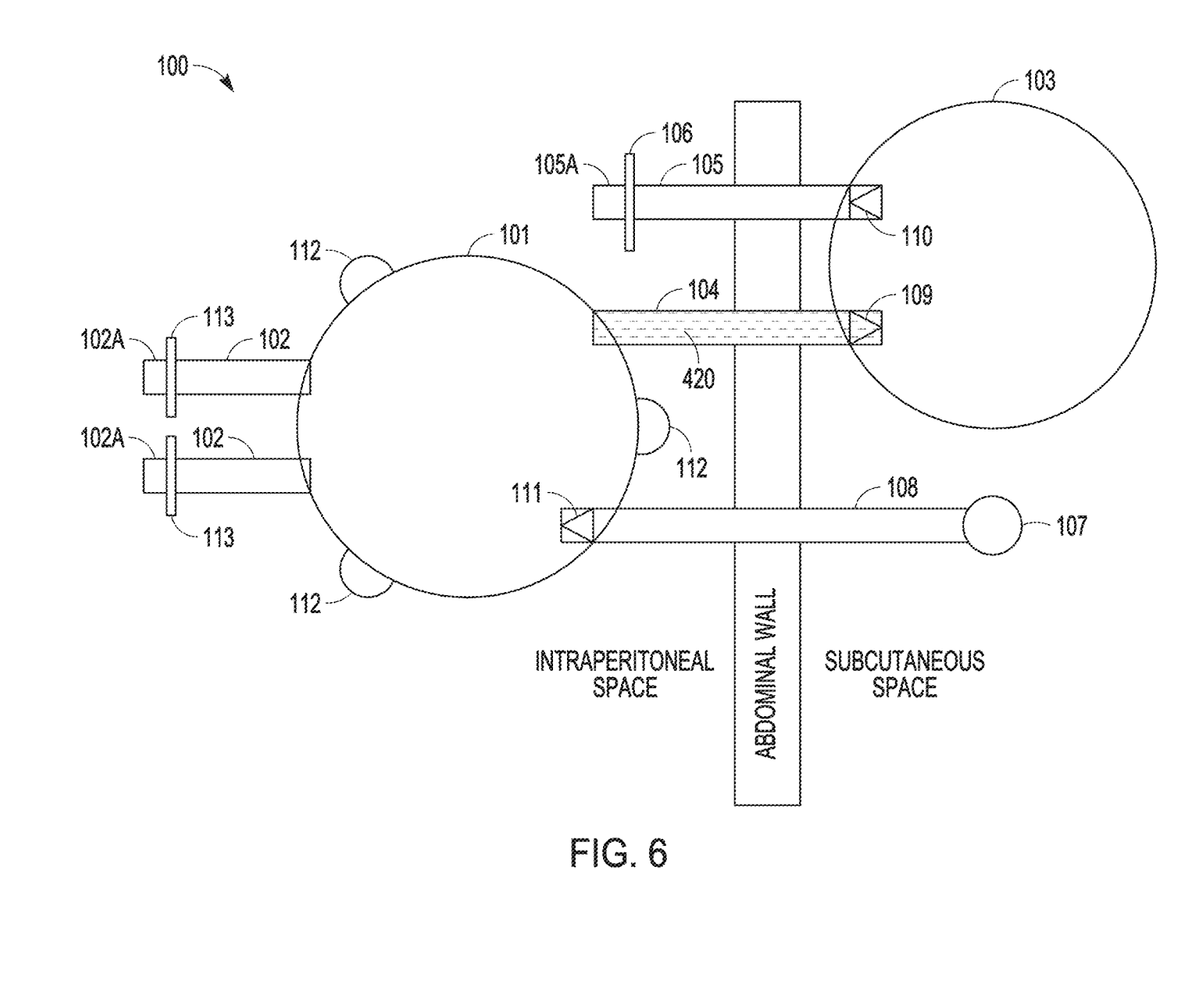
FIG. 6 shows a pump exerting a negative pressure to cause the urine to flow into the pump through a connection tube between the collection container and the pump.

FIG. 4 shows entrance of urine 420 into tubes 102 connected to the patient's ureters. FIG. 5 shows urine 420 reaches collection container 101, which is placed in the intraperitoneal space of the patient's abdominal cavity. FIG. 6 shows pump 103 exerting a negative pressure to cause urine 420 to flow into pump 103, which is placed in the subcutaneous space outside of the abdominal cavity, through tube 104 and unidirectional valve 109. Valve 109 prevents urine 420 from returning to collection container 101 after it reaches pump 103. FIG. 7 shows pump 103 being filled with urine 420. When pump 103 is substantially filled or fully filled, the patient can see and/or feel the need for urination. FIG. 8 shows the effect of external pressure applied on pump 103 to allow urine 420 to exit pump 103 and flow through tube 105 and unidirectional valve 110 for final expulsion of urine 420 through the patient's urethra. Valve 110 is opened under the pressure, such that urine flows from pump 103 to tube 105 only when pump 103 is under the external pressure, and prevents urine 420 from returning to pump 103 after it enters tube 105.

FIG. 9 shows cleaning port 107 being filled with liquid cleaning agent 922. The liquid cleaning agent can be injected into cleaning port 107 using a sharp hollow needle or lead that can pierce the wall of cleaning port 107, and the wall can be made self-sealing after being pierced. FIG. 10 shows liquid cleaning agent 922 enters collection container 101 through tube 108 and unidirectional valve 111. Valve 111 prevents liquid cleaning agent 922 from returning to tube 108 after it reaches collection container 101. FIG. 11 shows the entire interior space of the urination circuit (show by the shaded areas) of device 100 being washed using liquid wash agent 922. Once liquid cleaning agent 922 enters collection container 101, the process of washing and expulsion of liquid cleaning agent 922 resembles that of the urination cycle as illustrated in FIGS. 4-8.

The present subject matter is unique in terms of active support from the patient to expel the urine through the patient's natural, intact urethra. Once pump 103 is full or nearly full, the patient can see and/or feel it through the skin in the abdominal region. A gentle pressure with the fingers with the support from the abdominal muscle wall causes the expulsion of the urine.

The present subject matter provides a completely artificial and long-term stable bladder that does not require removal of part of the patient's intestine or other tissues of the patient, thus eliminating the associated risks, complications, and loss of performance over time. When compared to the use of an external bag attached to the abdomen, the present subject matter offers significant advantages in the patient's quality of life by, for example, solving problems associated with the external bag when participating in social activities.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. An implantable medical device for collecting and discharging urine from a body of a patient having kidneys, ureters, a urethra, an abdominal cavity, and abdominal muscles having a fascia, the implantable medical device comprising:
    first and second tubes configured to be connected to the ureters to receive the urine from the kidneys through the ureters;
    a collection container coupled to the first and second tubes and configured to be placed inside the abdominal cavity and to receive the urine from the first and second tubes;
    a pump configured to be placed outside of the abdominal cavity;
    a third tube connected between the collection container and the pump to provide for fluid communication from the collection container to the pump;
    a first unidirectional valve coupled to the third tube and configured to allow the urine to flow from the collection container to the pump;
    a fourth tube connected to the pump and configured to be connected to the urethra; and
    a second unidirectional valve coupled to the fourth tube and configured to allow the urine to flow from the pump to the urethra.

2. The implantable medical device of claim 1, wherein the collection container comprises flaps configured to be sutured to tissue of the body for fixation of the collection container.

3. The implantable medical device of claim 1, wherein the pump is configured to exert a negative pressure that opens the first unidirectional valve to allow the urine to flow from the collection container to the pump and closes the second unidirectional valve to prevent the urine from flowing from the pump to the urethra when the pump is not pressed.

4. The implantable medical device of claim 3, wherein the pump is configured to allow the patient to perceive a volume of the urine in the pump approaching a volume capacity of the pump and to exert a force that closes the first unidirectional valve to prevent the urine from flowing from the collection container to the pump and opens the second unidirectional valve to allow the urine to flow from the pump to the urethra when the pump is pressed.

5. The implantable medical device of claim 4, wherein the pump includes a hemispherical top portion and a flat base portion each having a wall, the base portion configured to be affixed to the fascia of the abdominal muscles, the wall of the flat base portion substantially thicker than the wall of the hemispherical top portion.

6. The implantable medical device of claim 1, further comprising:
    one or more first rings each coupled to the first tube and configured to be sutured to a first ureter of the ureters after a portion of the first tube is inserted into the first ureter;
    one or more second rings each coupled to the second tube and configured to be sutured to a second ureter of the ureters after a portion of the second tube is inserted into the second ureter; and
    one or more third rings coupled to the fourth tube and configured to be sutured to the urethra after a portion of the fourth tube is inserted into the urethra.

7. The implantable medical device of claim 1, further comprising:
    a cleaning port configured to be placed outside of the abdominal cavity and to receive a liquid cleaning agent;
    a fifth tube connected between the cleaning port and the collection container to allow fluid communication from the cleaning port to the collection container; and
    a third unidirectional valve coupled to the fifth tube and configured to allow the liquid cleaning agent to flow from the cleaning port to the collection container.

8. The implantable medical device of claim 7, wherein the cleaning port is configured to be pierced by a hollow needle, to receive the liquid cleaning agent by injection through the hollow needle, and to self-seal upon removal of the hollow needle.

9. The implantable medical device of claim 1, wherein the implantable medical device is made of biocompatible elastic material.

10. The implantable medical device of claim 9, wherein the implantable medical device is entirely made of medical grade silicone.

11. An implantable medical device for collecting and discharging a fluid and for being cleaned using a liquid cleaning agent, the implantable medical device comprising:
    first and second tubes configured to receive the fluid;
    a collection container coupled to the first and second tubes and configured to receive the fluid from the first and second tubes;
    a pump;
    a third tube connected between the collection container and the pump to provide for fluid communication from the collection container to the pump;
    a first unidirectional valve coupled to the third tube and configured to allow the fluid to flow from the collection container to the pump;
    a fourth tube connected to the pump;
    a second unidirectional valve coupled to the fourth tube and configured to allow the fluid to flow from the pump to the fourth tube;
    a cleaning port configured to receive the liquid cleaning agent;
    a fifth tube connected between the cleaning port and the collection container to allow fluid communication from the cleaning port to the collection container; and
    a third unidirectional valve coupled to the fifth tube and configured to allow the liquid cleaning agent to flow from the cleaning port to the collection container.

12. The implantable medical device of claim 11, wherein the implantable medical device is entirely made of medical grade silicone.

13. A method for replacing functions of a urinary bladder using an implantable medical device placed in a body of a patient having kidneys, ureters, a urethra, an abdominal cavity, and abdominal muscles having a fascia, the method comprising:
  collecting urine from kidneys of the body using a collection container placed within the abdominal cavity through first and second tubes connected between the ureters and the collection container;
  allowing the urine to flow from the collection container to a pump subcutaneously placed outside of the abdominal cavity through a third tube connected between the collection container and the pump when the pump is not pressed by the patient; and
  allowing the urine to flow from the pump to the urethra through a fourth tube connected between the pump and the urethra when the pump is pressed by the patient.

14. The method of claim 13, further comprising constructing the collection container, the pump, and the first, second, third, and fourth tubes using a biocompatible elastic material.

15. The method of claim 14, further comprising constructing the implantable medical device entirely using medical grade silicone.

16. The method of claim 13, further comprising configuring the pump to allow the patient to perceive fullness of the pump as an indication of need for urination.

17. The method of claim 16, further comprising provide the patient with a volume capacity of each of the collection container and the pump determined for the patient.

18. The method of claim 13, further comprising introducing a liquid cleaning agent into the collection container for cleaning interior space of the implantable medical device.

19. The method of claim 18, wherein introducing the liquid cleaning agent into the collection container comprises injecting the liquid cleaning agent into a cleaning port subcutaneously placed outside of the abdominal cavity and connected to the collection container through a fifth tube.

20. The method of claim 19, wherein introducing the liquid cleaning agent comprises introducing one or more substances that disinfects and prevents bladder stone formation.

* * * * *